United States Patent
Just et al.

(10) Patent No.: US 8,333,732 B2
(45) Date of Patent: Dec. 18, 2012

(54) SEAL FOR CONTROLLING IRRIGATION IN BASKET CATHETERS

(75) Inventors: Dale E. Just, Minneapolis, MN (US); James V. Kauphusman, Champlin, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/099,715

(22) Filed: May 3, 2011

(65) Prior Publication Data

US 2011/0208165 A1 Aug. 25, 2011

Related U.S. Application Data

(63) Continuation of application No. 12/345,598, filed on Dec. 29, 2008, now Pat. No. 7,955,299.

(51) Int. Cl.
*A61M 29/00* (2006.01)

(52) U.S. Cl. .................................. 604/99.01

(58) Field of Classification Search .......... 604/105–109, 604/246, 509, 103.01–103.03, 103.05, 99.01; 606/192, 194; 600/374
See application file for complete search history.

(56) References Cited

U.S. PATENT DOCUMENTS

| | | | |
|---|---|---|---|
| 5,178,608 A * | 1/1993 | Winters | 604/102.02 |
| 5,647,870 A | 7/1997 | Kordis et al. | |
| 5,855,552 A | 1/1999 | Houser et al. | |
| 5,871,483 A | 2/1999 | Jackson et al. | |
| 5,893,847 A | 4/1999 | Kordis | |
| 5,925,038 A | 7/1999 | Panescu et al. | |
| 5,928,228 A | 7/1999 | Kordis et al. | |
| 6,096,055 A * | 8/2000 | Samson | 606/194 |
| 6,119,030 A | 9/2000 | Morency | |
| 6,280,414 B1 * | 8/2001 | Shah et al. | 604/104 |
| 6,741,878 B2 | 5/2004 | Fuimaono et al. | |
| 6,748,255 B2 | 6/2004 | Fuimaono et al. | |
| 6,973,340 B2 | 12/2005 | Fuimaono et al. | |
| 7,149,563 B2 | 12/2006 | Fuimaono et al. | |
| 7,257,434 B2 | 8/2007 | Fuimaono et al. | |
| 2003/0114739 A1 | 6/2003 | Fuimaono et al. | |
| 2004/0133091 A1 | 7/2004 | Fuimaono et al. | |
| 2006/0009690 A1 | 1/2006 | Fuimaono et al. | |
| 2007/0276212 A1 | 11/2007 | Fuimaono et al. | |
| 2009/0192453 A1* | 7/2009 | Wesselmann | 604/101.01 |

* cited by examiner

*Primary Examiner* — Christopher D Koharski
(74) *Attorney, Agent, or Firm* — Trenner Law Firm LLC

(57) ABSTRACT

An exemplary basket catheter includes an outer tubing housing an inner fluid delivery tubing having at least one fluid delivery port. A plurality of splines are each connected at a proximal end of the splines to the outer tubing and at a distal end of the splines to the inner fluid delivery tubing. The inner fluid delivery tubing is operable to be moved in a first direction to expand the splines; and in a second direction to collapse the splines. A porous membrane is provided over at least a portion of the inner fluid delivery tubing. A seal is provided at a proximal end of the porous membrane between the porous membrane and the outer tubing and between the porous membrane and the inner fluid delivery tubing, the seal configured for irrigating between the plurality of splines of the basket catheter while preventing fluid ingress into the outer tubing.

20 Claims, 6 Drawing Sheets

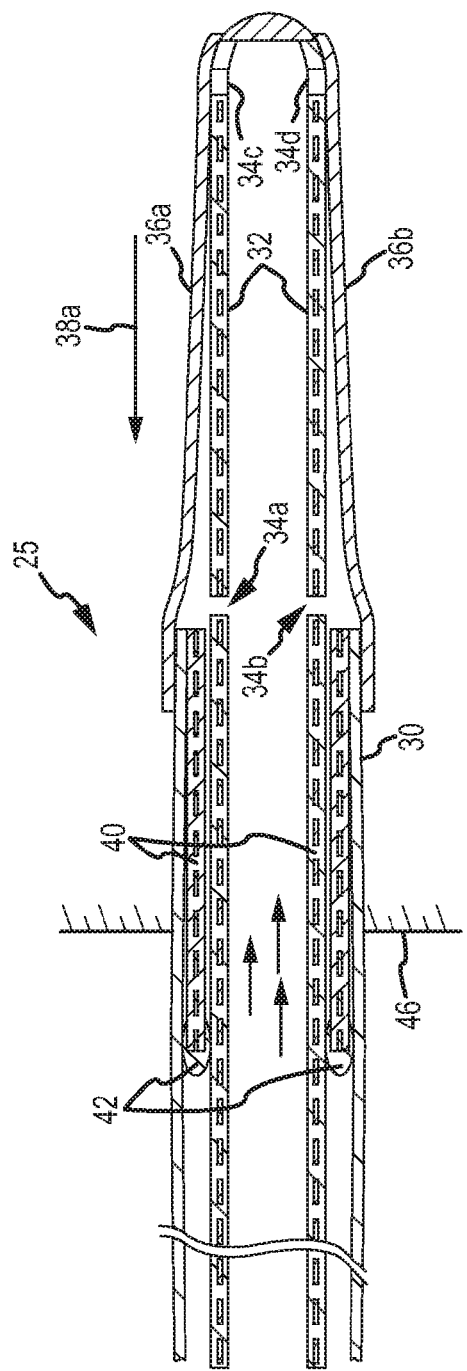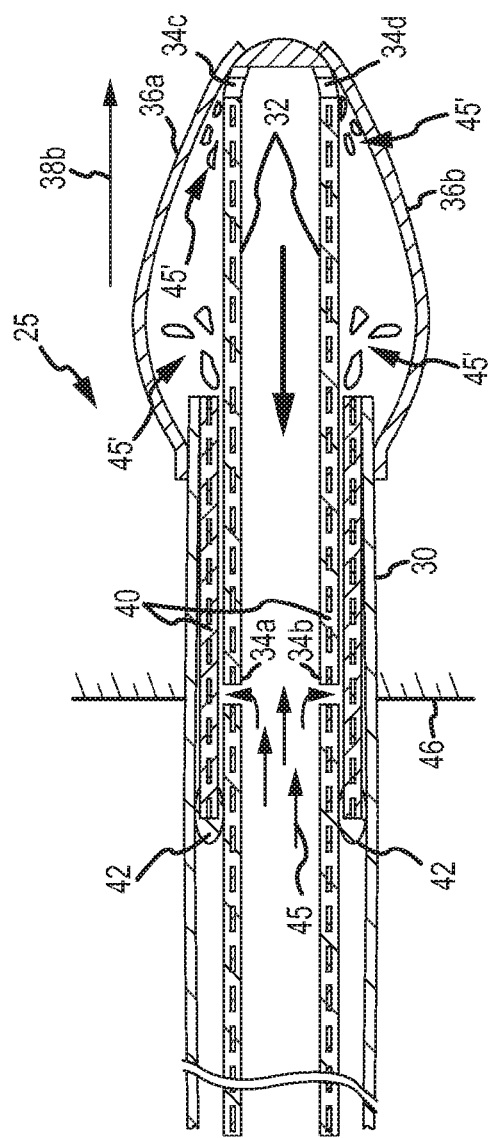

SEAL FOR CONTROLLING IRRIGATION IN BASKET CATHETERS

CROSS-REFERENCE TO RELATED APPLICATIONS

This application is a continuation of U.S. application Ser. No. 12/345,598, filed 29 Dec. 2008 now U.S. Pat. No. 7,955,299 (the '598 application), now pending. The '598 application is hereby incorporated by reference as though fully set forth herein.

BACKGROUND OF THE INVENTION a. Field of the Invention

The instant invention is directed toward a mechanical seal for controlling delivery of a fluid (e.g., an anticoagulant) for irrigation in basket catheters. In particular, the mechanical seal of the present invention may be used to help direct the fluid between splines of the basket catheter, especially at the apexes, while preventing fluid ingress into the body of the catheter to assist in preventing thrombus formation without inhibiting axial movement of a deployment mechanism for the basket catheter.

b. Background Art

Normal heart rhythm is between 60 and 100 beats per minute. Tachycardia is a fast heart rate (usually over 100 beats per minute) caused by disease or injury. Tachycardias may begin in the upper chambers of the heart (the atria) or the lower chambers of the heart (the ventricles). Some tachycardias are harmless, but other tachycardias are life threatening. Tachycardias can deteriorate to fibrillation, a disorder in which, the heart does not move enough blood to meet the needs of the body.

Atrial fibrillation (AF) is the most common abnormal heart rhythm. It is a very fast, uncontrolled heart rhythm that occurs when the upper chambers of the heart (the atria) try to beat so fast (between 350 and 600 times per minute) that they only quiver. Ventricular fibrillation (VF) occurs when the lower chambers of the heart (the ventricles) produce fast and erratic electrical impulses that fail to induce synchronous mechanical contraction, such that oxygenated blood is not circulated through the body. Fibrillation in the ventricles is a life-threatening arrhythmia demanding immediate treatment.

Before a tachycardia deteriorates to fibrillation, various procedures may be used to treat the heart tissue and reduce or altogether eliminate the occurrence of fibrillations. It is well known that treatment benefits may be gained by creating lesions in the heart tissue, which change the electrical properties of the tissue, if the depth and location can be controlled. For example, cardiac ablation techniques are known for forming lesions at specific locations in cardiac tissue to lessen or eliminate undesirable atrial fibrillations. Likewise, biologic and chemical agents may be delivered into infracted tissue in the lower chambers of the heart (the ventricles) to promote angiogenesis for the treatment of Ventricular Tachycardia (VT). Other procedures are also known for treating these and other ailments. Use of a particular procedure depends at least to some extent on the desired treatment, and may also depend on other considerations, such as tissue characteristics.

A basket catheter may be employed for ablation and other procedures (e.g., mapping) of the heart. The catheter system may include an outer catheter shaft also referred to as a "guiding introducer". The guiding introducer defines at least one lumen or longitudinal channel. A delivery sheath is fitted through the guiding introducer. To pre-position the sheath at the appropriate location in the heart, a dilator is first fitted through the sheath. In an example of a procedure within the left atrium, the sheath and the dilator are first inserted in the femoral vein in the right leg. The sheath and dilator are then maneuvered up to the inferior vena cava and into the right atrium. In what is typically referred to as a transseptal approach, the dilator is pressed through the interatrial septum between the right and left atria. A dilator needle may be used here to make an opening for the dilator to pass through. The dilator expands the opening sufficiently so that the sheath may then be pressed through the opening to gain access to the left atrium and the pulmonary veins. With the sheath in position, the dilator is removed and the basket catheter, needle, or other device (depending on the procedure) is fed into the lumen of the sheath and pushed along the sheath into the left atrium. When positioned in the left atrium, various mapping and/or ablation procedures, such as the ablation procedures described above, may be performed within the heart.

Several difficulties may be encountered, however, during these procedures using some existing basket catheters. For example, when the basket catheter is expanded within the heart for a procedure, and then collapsed again (e.g., to move to another location within the heart), a slowing or stoppage of the flow blood may occur between the splines of the basket catheter, especially at or near the apexes where the splines are attached to the catheter. This slowing or stoppage of the flow of blood may result in blood clot formation and may possibly lead to a thrombus. A thrombus may decrease blood flow or even completely cut off blood flow, resulting in heart attack or stroke. Indeed, the risk of thrombus formation continues to exist even after the basket catheter has been removed following the procedure.

Thus, there remains a need for preventing thrombus while enabling movement of the catheter shaft during a procedure.

BRIEF SUMMARY OF THE INVENTION

It is desirable to be able to deliver an anticoagulant (e.g., heparinized saline) or other fluid between the splines of a basket catheter during various procedures on the heart in order to reduce the risk of thrombus formation. It is further desirable to be able to maintain a hemostatic seal at a distal end of the catheter for delivering the anticoagulant or other fluid without fluid ingress into the catheter shaft so that the fluid can be better directed between the splines of the basket catheter. It is still further desirable to be able to do all of this while retaining the ability to axially move a deployment mechanism, e.g., for a basket catheter.

These and other objectives can be accomplished by the catheter systems and methods disclosed herein for conveying an anticoagulant or other fluid between the splines of a basket catheter, especially at or near the apexes where the splines are attached to the catheter. A seal for use with the catheters is configured to reduce or altogether prevent fluid ingress into the patient's body while still retaining the ability to axially move a deployment mechanism of the catheter, e.g., for the basket catheter.

An exemplary basket catheter includes an outer tubing housing an inner fluid delivery tubing having at least one fluid delivery port. A plurality of splines each connected at a proximal end of the splines to the outer tubing and at a distal end of the splines to the inner fluid delivery tubing. The inner fluid delivery tubing is operable to be moved in a first direction relative to the outer tubing to expand the splines to a deployed position. The inner fluid delivery tubing is also operable to be moved in a second direction relative to the outer tubing to collapse the splines to an undeployed position. A porous membrane is provided over at least a portion of the inner fluid delivery tubing having the at least one fluid delivery port. A seal is provided at a proximal end of the porous membrane between the porous membrane and the outer tubing and between the porous membrane and the inner fluid delivery tubing, the seal configured for irrigating between the splines of the basket catheter while preventing fluid ingress into the catheter shaft.

An exemplary catheter system includes a guiding introducer housing a delivery sheath, and a basket catheter insertable through the guiding introducer. The basket catheter includes an outer tubing housing an inner fluid delivery tubing, and a plurality of splines operable to be moved to a deployed position and an undeployed position. A porous membrane is provided within the outer tubing of the basket catheter over a fluid delivery port formed in a portion of the inner fluid delivery tubing of the basket catheter. A seal is molded to the porous membrane, the seal configured for irrigating between the splines of the basket catheter, while permitting movement of the fluid delivery tube to move the splines and preventing fluid ingress into the catheter shaft.

Another exemplary catheter system for delivering an anticoagulant or other fluid includes an outer shaft housing a delivery sheath, and a basket catheter insertable through the outer shaft. The basket catheter includes an outer tubing housing an inner fluid delivery tubing, and a plurality of splines each connected at a proximal end of the splines to the outer tubing and at a distal end of the splines to the inner fluid delivery tubing. The inner fluid delivery tubing is operable to be moved in a first direction relative to the outer tubing to expand the splines to a deployed position. The inner fluid delivery tubing is also operable to be moved in a second direction relative to the outer tubing to collapse the splines to an undeployed position. A porous membrane sealed between the outer tubing of the basket catheter and the inner fluid delivery tubing of the basket catheter. The porous membrane configured for irrigating between the splines of the basket catheter with the anticoagulant, while permitting movement of the fluid delivery tube to move the splines.

The foregoing and other aspects, features, details, utilities, and advantages of the present invention will be apparent from reading the following description and claims, and front reviewing the accompanying drawings.

BRIEF DESCRIPTION OF THE DRAWINGS

FIG. 2a is a cross-sectional view of the tip portion of the sheath in FIG. 2 showing the basket catheter with the splines in the collapsed position.

FIG. 3a is a cross-sectional view of the tip portion of the sheath in FIG. 2 showing the basket catheter with the splines in the expanded position.

DETAILED DESCRIPTION OF THE INVENTION

Several embodiments of a catheter system according to the present invention are depicted in the figures as the catheter system may be used for delivery of an anticoagulant (e.g., heparinized saline) or other fluid between the splines of a basket catheter, especially at or near the apexes where the splines are attached to the catheter, in order to reduce the risk of thrombus formation during a medical procedure. As described further below, the catheter of the present invention provides a number of advantages, including, for example, facilitating delivery of the anticoagulant or other fluid to reduce thrombus formation without ingress of fluid into the catheter shaft. These advantages are realized without interfering with an actuating mechanism for a basket catheter.

Before continuing, it is noted that other components typical of systems which are conventionally implemented for such procedures, are not shown or described herein for purposes of brevity. Such components may nevertheless also be provided as part of, or for use with, the catheter. For example, catheter systems commonly include or are used in conjunction with an ECG recording system, and/or various input and output devices. Such components are well understood in the medical devices arts and therefore further explanation is not necessary for a complete understanding of the invention.

Figure 1:
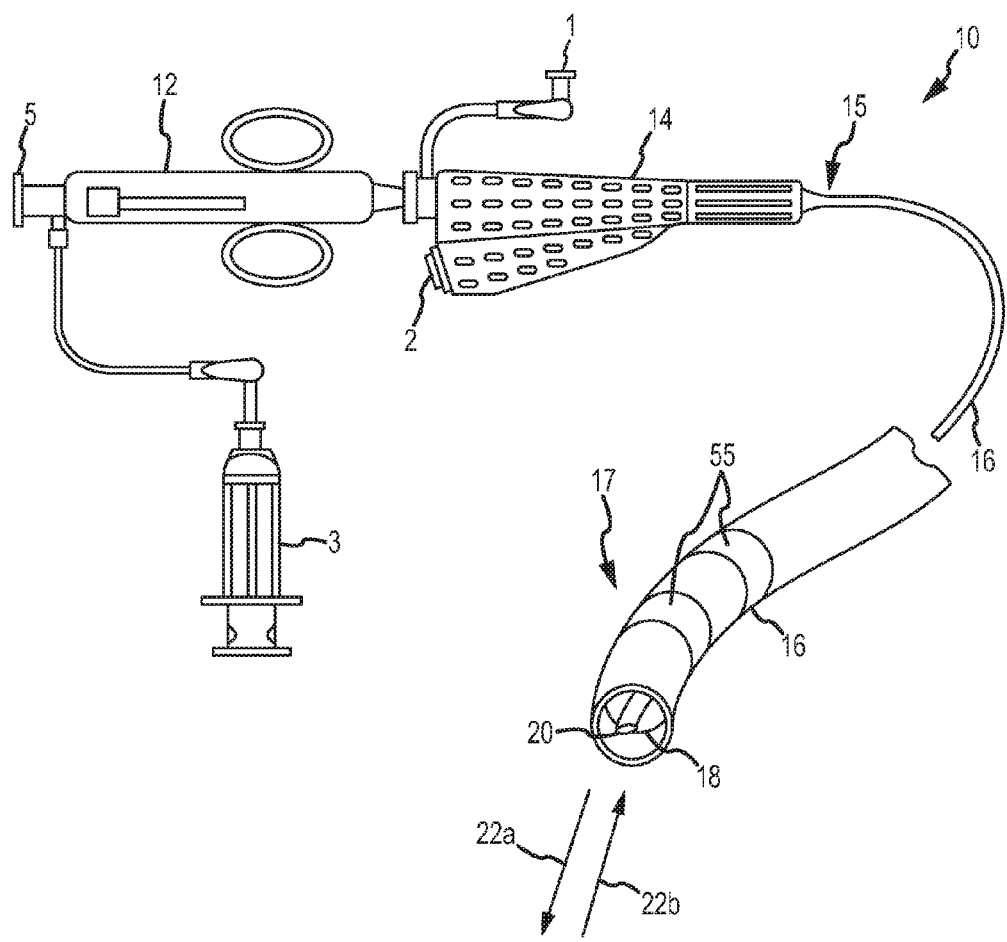
FIG. 1 is a perspective view of an exemplary embodiment of a catheter system.
Figure 1A:
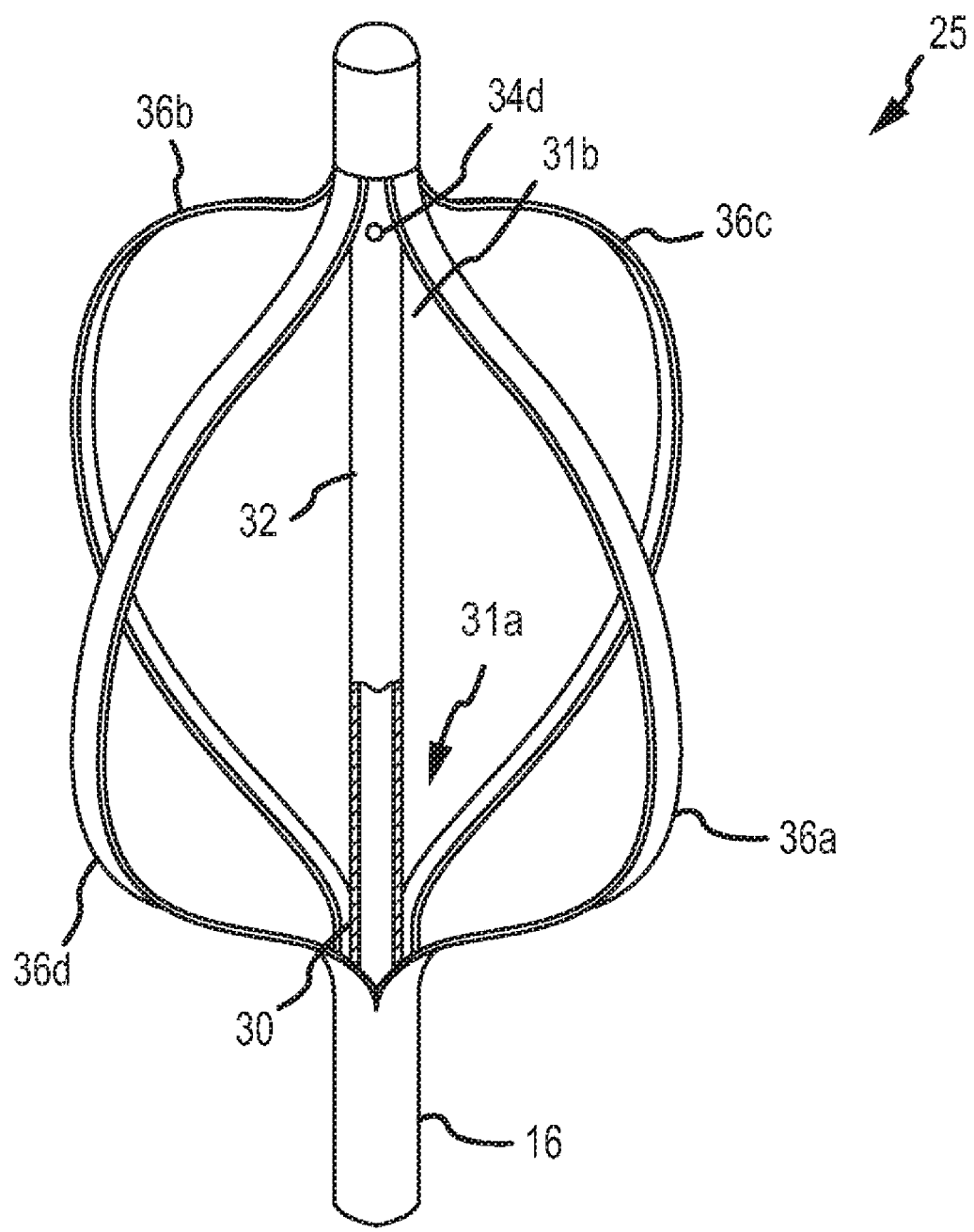
FIG. 1a is a perspective view of an exemplary embodiment of a basket catheter which may be implemented with the catheter system in FIG. 1.

FIG. 1 is a perspective view of an exemplary embodiment of a catheter system 10 which may implement fluid delivery means for conveying an anticoagulant or other fluid between splines of a basket catheter 25, especially at or near the apexes 31a, 31b where the splines are attached to the catheter. FIG. 1a is a perspective view of an exemplary embodiment of a basket catheter 25 which may be implemented with the catheter system 10 in FIG. 1. The catheter system 10 may include a handle 12 and connector 14 at the base or proximal end 15. An outer catheter shaft also referred to as a "guiding introducer" 16 having a tubular body is connected to the connector 14 on the proximal end (e.g., illustrated by reference number 15 in FIG. 1) of the catheter system 10. As used herein and commonly used in the art, the term "proximal" is used generally to refer to components or portions of the catheter system 10, such as the handle 12 and connector 14 that are located or generally orientated away from or opposite the heart or other target tissue when the catheter system 10 is in use. On the other hand, the term "distal" (e.g., illustrated in FIG. 1 by reference number 17) is used generally to refer to components located or generally orientated toward the heart or other target tissue when the catheter system 10 is in use.

The guiding introducer 16 defines at least one lumen or longitudinal channel. A delivery sheath 18 is fitted through the guiding introducer 16. In one implementation, the guiding introducer 16 and sheath 18 are fabricated from a flexible resilient material, and are preferably fabricated of materials suitable for use in humans, such as nonconductive polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. Some portions of the guiding introducer 16 and/or sheath 18 may be braided for enhanced stiffness and torqueability.

In exemplary implementations, the guiding introducer 16 and sheath 18 are each about two to four feet long, so that they may extend from the left atrium through the body and out of the femoral vein in the right leg and be connected with various catheter devices such as the connector 14, one or more fluid control valves 1-3, and the like.

The sheath 18 is configured to receive and guide a device for carrying out the procedure (e.g., the basket catheter 25 shown in FIG. 1a, FIG. 2-2a, and 3-3a within the lumen to the target tissue. The sheath 18 is pre-positioned in the appropriate location in the heart prior to introduce a device. To pre-position the sheath 18 at the appropriate location in the heart, a dilator 20 is first fitted through the sheath 18. In an example of a procedure within the left atrium, the sheath 18 and the dilator 20 are first inserted in the femoral vein in the right leg. The sheath 18 and dilator 20 are then maneuvered up to the inferior vena cava and into the right atrium. In what is typically referred to as a transseptal approach, the dilator 20 is pressed through the interatrial septum between the right and left atria. A needle may be used here to make an opening for the dilator 20 to pass through. The dilator expands the opening sufficiently so that the sheath 18 may then be pressed through the opening to gain access to the left atrium and the pulmonary veins. With the sheath 18 in position, the dilator 20 is removed and the basket catheter 25 (FIG. 1a) may be fed into the lumen of the sheath 18 and pushed along the sheath 18 into the left atrium. When positioned in the left atrium, various procedures (e.g., ablation and mapping procedures) may be performed within the heart tissue using the basket catheter.

Once the sheath 18 is pre-positioned in the appropriate location in the heart, the basket catheter 25 may be at least partially extended out from the lumen at the distal end 17 of the sheath 18 in the direction illustrated by arrow 22a) so that the basket catheter 25 may be positioned adjacent the target tissue, and then expanded for the medical diagnostic procedure. The basket catheter 25 may also be collapsed and then retracted (e.g., in the direction of arrow 22b) before removing the catheter system 10 from the body.

Before continuing, it is noted that the catheter system 10 has been described as it may be inserted for procedures in the left atrium in the vicinity of or within the pulmonary veins of the heart. The catheter system 10, however, is not limited to such procedures, and may be used for procedures involving other target tissue in other areas of the heart and body.

The following discussion will now be with reference to the basket catheter 25 shown in FIG. 1a, and more particularly with reference to the details shown in FIGS. 2 and 2a and FIGS. 3 and 3a. In these figures, an exemplary basket catheter 25 is shown as it may include an outer tubing 30 housing an inner fluid delivery tubing 32 having at least one fluid delivery port 34a-d near the apexes 31a,b (shown in FIGS. 2a and 3a). The basket catheter 25 may also include a plurality of splines 36a-d (although only two of the splines 36a, 36b are visible in FIGS. 2 and 2a, and in FIGS. 3 and 3a). The portion on either end of the basket catheter 25 where the splines 36a-d are attached to the catheter are referred to herein as the apexes 31a, b. Fluid deliver ports 34a-d may be positioned at or near the apexes. It is noted that although fluid delivery ports 34a-d and splines 36a-d are shown in the drawings, the basket catheter 25 is not limited to any particular configuration (including number of splines or number or placement of ports), as will be readily understood by those having ordinary skill in the art after becoming familiar with the teachings herein.

Figure 2:
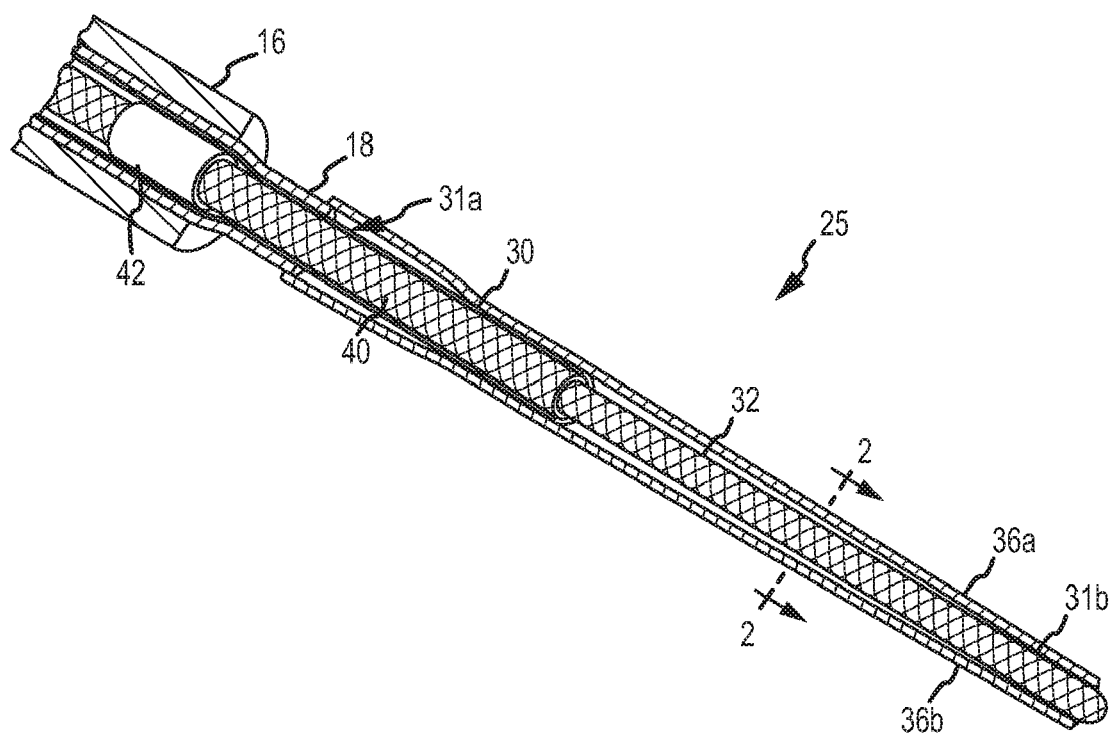
FIG. 2 is a perspective view of a tip portion of a sheath showing an exemplary embodiment of a basket catheter, wherein the splines of the basket catheter are in a collapsed position.
Figure 3:
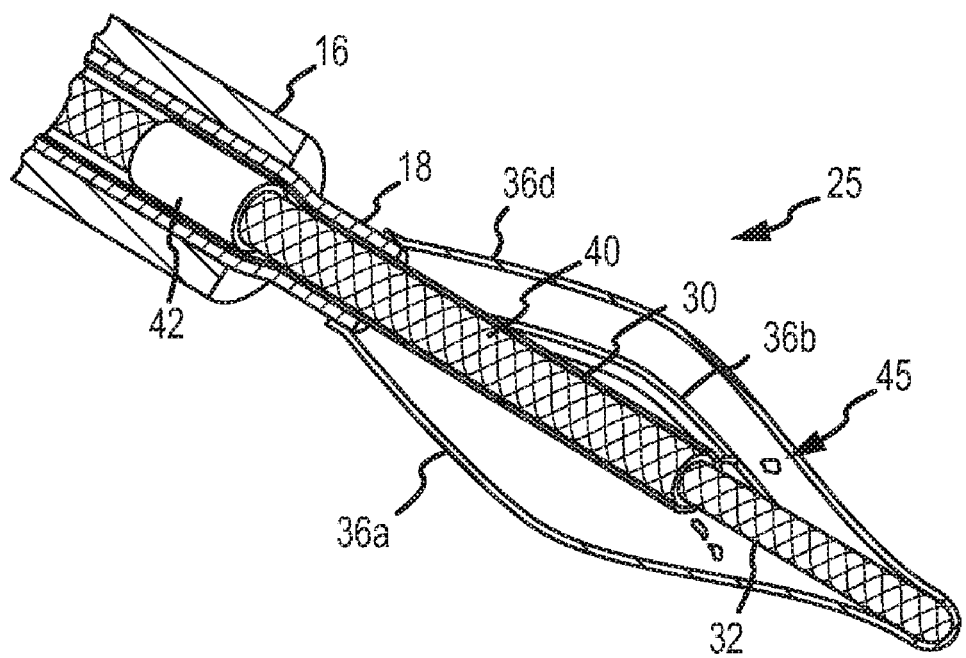
FIG. 3 is a perspective view of a tip portion of a sheath showing an exemplary embodiment of a basket catheter, wherein the splines of the basket catheter are in an expanded position.

Each spline 36a-d is connected at the proximal end of the splines 36a-d to the sheath 18. In addition, each spline 36a-d is connected at the opposite or distal end of the splines 36a-d to the inner fluid delivery tubing 32. The inner fluid delivery tubing 32 is thus operable to be moved in a first direction (e.g., in the direction of arrow 38a in FIG. 2a) relative to the sheath 18 to expand the splines 36a-d to a deployed position, as shown in FIGS. 3 and 3a. The inner fluid delivery tubing 32 is also operable to be moved in a second direction (e.g., in the direction of arrow 38b in FIG. 3a) relative to the sheath 18 to collapse the splines 36a-d to an undeployed position, as shown in FIGS. 2 and 2a. For example, the splines 36a-d may be moved to the undeployed position following the procedure so that the basket catheter 25 may be withdrawn through the delivery sheath 18 and guiding introducer 16 of the catheter 10.

A basket deployment system may be implemented to control deployment of the splines 36a-d. The basket deployment system may be connected to any of a wide variety of catheter systems (e.g., to port 5 on the handle 12 of catheter system 10 shown in FIG. 1). The basket deployment system includes a handle portion operatively associated with the inner fluid delivery tubing 32 in such a manner that movement of the handle is directly translated into movement of the inner fluid delivery tubing 32. During operation, the inner fluid delivery tubing 32 moves in the direction of arrow 38a in FIG. 3a when the handle is retracted or otherwise pulled back, thereby deploying the splines 36a-d. Likewise, the inner fluid delivery tubing 32 moves in the direction of arrow 38b when the handle is returned toward its starting position, thereby collapsing the splines 36a-d.

In an exemplary embodiment, the handle may be spring-loaded (not shown). The spring acts to bias the handle in a fully extended or pulled back position. A force must be applied to the handle in order to release the handle, and hence return the inner fluid delivery tubing 32 toward its starting position. This may help ensure that the user does not leave the splines 36a-d of the basket in an expanded position when attempting removal of the catheter system from the patient's body. This may also help ensure that the basket is not accidentally deployed during placement of the catheter system in the patient's body (doing so could cause unintended damage to tissue or other parts of the patient's body).

Other embodiments of deployment systems are also contemplated and are not limited to the specific implementation described above. For example, different mechanisms for controlling the distance the inner fluid delivery tubing 32 can travel may be implemented.

The basket catheter 25 may also include a membrane 40 provided over at least a portion of the inner fluid delivery tubing having the at least one fluid delivery port. In an exemplary embodiment, the porous membrane 40 is manufactured of a braided material such as, commercially available braided polyimide tubing. A porous membrane permits fluid egress delivered through fluid delivery ports 34a-d from in between the inner fluid delivery tubing 32 and the porous membrane. However, the membrane 40 is not limited to use with porous materials.

A seal 42 is provided at a proximal end of the membrane 40. For example, the seal 42 may be molded to the membrane 40. The seal 42 may be juxtapositioned on one side between the membrane 40 and the outer tubing 30, and on the other side between the membrane 40 and the inner fluid delivery tubing 32. The seal 40 may have an inner diameter which is smaller than the outer diameter of the inner fluid delivery tubing. In addition, the seal 40 may have an outer diameter larger than the inner diameter of the outer tubing. The specific diameters may vary depending on a number of design considerations, such as, the diameter of the outer sheath 18 or other components of the catheter 10. Sizing the diameters in such a manner enables the seal 40 to provide a snug fit between the respective tubing 30 and 32, and the membrane 40. Accordingly, fluid traveling through fluid delivery tube 32 (e.g., in the direction of arrows 45) is forced out through the distal end of the membrane 40 (e.g., as illustrated in FIGS. 3 and 3a by discharged fluid 45) for irrigating between the splines 36a-d of the basket catheter 25. The seal prevents fluid ingress back within the catheter shaft so that the apexes are effectively irrigated.

The seal 40 may be manufactured of any suitable material. In an exemplary embodiment, the seal 40 may be manufactured of a low durometer material, such as rubber, although plastic, metal or other material may also be used. When a low durometer material is put under pressure the material has a "memory" (tending back toward its original shape), enabling a seal under little or even no pressure. In any event, the seal 40 may be made of a material that enables the seal 40 to prevent fluid ingress outside of the heart wall white still permitting movement of the fluid delivery tube 32 in the first and second directions 38a and 38b, respectively, so that the splines can still be expanded and collapsed.

In an exemplary embodiment, at least one axial support may be provided between the inner fluid delivery tubing 32 and the membrane 40. The axial support is configured for fluid flow between the inner fluid delivery tubing and the porous membrane. The axial support is also configured to provide mechanical support for maintaining the inner fluid delivery tubing 32 substantially centered within the membrane 40.

The seal 40 may be manufactured of any suitable material. In an exemplary embodiment, the seal 40 may be manufactured of a low durometer material, such as rubber, although plastic, metal or other material may also be used. When a low durometer material is put under pressure the material has a "memory" (tending back toward its original shape), enabling a seal under little or even no pressure. In any event, the seal 40 may be made of a material that enables the seal 40 to prevent fluid ingress outside of the heart wall while still permitting movement of the fluid delivery tube 32 in the first and second directions 38a and 38b, respectively, so that the splines can still be expanded and collapsed.

Figure 4A:
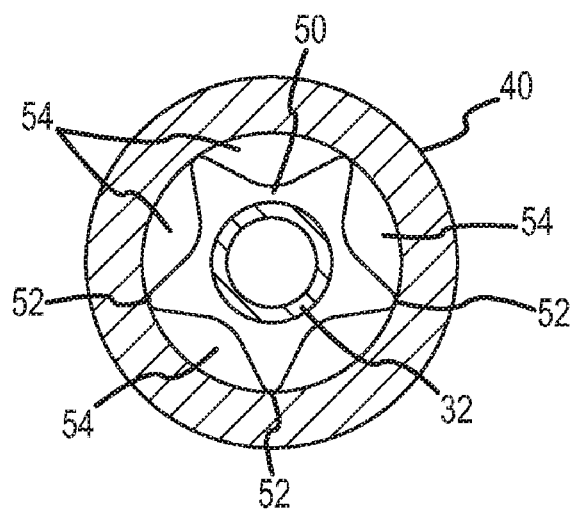
FIG. 4a is a cross-sectional view taken along lines 2-2 in FIG. 2 showing an exemplary support structure which may be implemented to provide mechanical support for the inner fluid delivery tubing within the membrane.
Figure 4B:
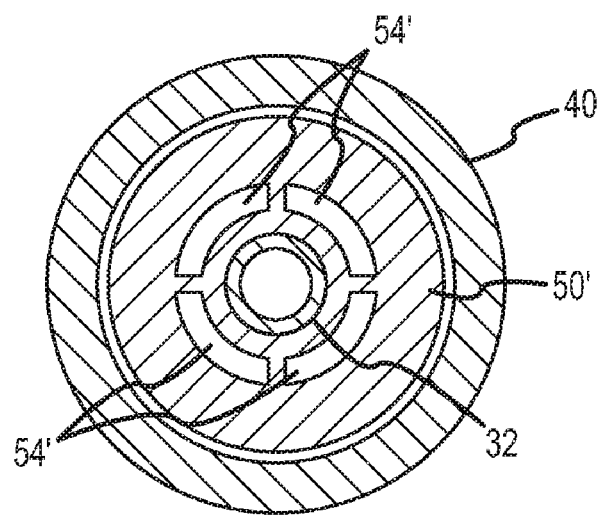
FIG. 4b is a cross-sectional view of an alternative exemplary embodiment of a support structure which may be implemented to provide mechanical support for the inner fluid delivery tubing within the membrane.

FIG. 4b is a cross-sectional view of an alternative exemplary embodiment of an axial support structure 50' which may be implemented between the inner fluid delivery tubing 32 and the membrane 40. In this embodiment, the support structure 50' is substantially radial-shaped. This embodiment also maintains the inner fluid delivery tubing 32 approximately in the center of the membrane 40.

The support structure 50 or 50' may include one or more interstitial spaces (e.g., spaces 54 or 54' formed by the support structure as shown in FIG. 4a-b). These interstitial spaces enable the fluid dispensed through ports 34a-d of the inner fluid delivery tubing through the space defined between the inner fluid delivery tubing 32 and the membrane 40 and to be discharged, e.g., as shown in FIGS. 3 and 3a.

It should be noted that although the cross-section shown in FIG. 4a-b is depicted as a circular cross-section, it is noted that the cross-section may intentionally or unintentionally have a wide variety of cross-sectional configurations and areas, and need not be circular. For example, manufacturing irregularities may result in different cross-sectional configurations. Or for example, different cross-sectional configurations may be intentionally selected to achieve desired properties.

Of course other designs of the support structure may also be implemented as will be readily understood by those having ordinary skill in the art after becoming familiar with the teachings herein. It is noted that the support structure need not maintain the inner fluid delivery tubing in the center of the membrane 40. It is only desired that the inner fluid delivery tithing be maintained in a substantially constant position within the diameter of the membrane 40 for uninterrupted flow of the fluid during the procedure.

The particular types and configuration of support structure used will depend at least to some extent on design considerations. Exemplary design considerations may include, but are not limited to, the material and desired structural properties, the length, shape, and cross-sectional area of the sheath. And of course, the design parameters may be different for various procedures or physician preferences.

It is noted that the various embodiments of catheter system 10 described above with reference to the figures may also be implemented with a wide variety of different sensors. In an exemplary embodiment, the catheter system 10 may include one or more piezoelectric sensor embedded in the sheath 18 or the splines 36a-d. The piezoelectric sensor generates electric signals in response to stresses caused by contact with the tissue. Radiopaque sensors may also be used. Still other exemplary sensing devices may include pressure, thermistor, thermocouple, or ultrasound sensors. In addition, more than one sensor or type of sensor may be implemented to provide additional feedback to the user. In any event, when the sheath 18 or the splines 36a-d are positioned in contact with and/or moved over a tissue, the sensors may be implemented to generate an electrical signal corresponding to stress caused by this contact and/or movement for tissue contact assessment.

Electrical wiring (not shown) may also extend through the lumen of the catheter system 10 to enable these sensors. The electrical wiring may convey electrical signals from the sensor(s) to a data acquisition/processing/output device (also not shown), such as, e.g., an echocardiogram (ECG) device. Alternatively, a wireless connection my be implemented, e.g., by providing a transmitter in the catheter and a receiver in association with the data acquisition/processing/output device. Accordingly, the electrical signals from the sensor(s) may be viewed by the user, e.g., as output on an electrical monitoring device. The resulting electrical signal may be processed and/or otherwise output for the user so that the user is able to assess tissue contact by the catheter system 10.

It is noted that any suitable analog and/or digital device may be implemented for outputting the electrical signals generated by the sensor(s) to a user. In addition, the electrical signals may be further characterized using a suitable processing device such as, but not limited to, a desktop or laptop computer. Such processing device may be implemented to receive the voltage signal generated by the contact assessment sensor(s) and convert it to a corresponding contact condition and output for the user, e.g., at a display device, an audio signal, or tactile feedback or vibrations on the handle of the catheter. In any event, circuitry for conveying output of the piezoelectric sensor to a user in one form or another may be readily provided by those having ordinary skill in the electronics arts after becoming familiar with the teachings herein.

Electrical wiring (not shown) may also extend through the lumen of the catheter system 10 to enable these sensors. The electrical wiring may convey electrical signals from the sensor(s) to a data acquisition/processing/output device (also not shown), such as, e.g., an echocardiogram (ECG) device. Alternatively, a wireless connection may be implemented, e.g., by providing a transmitter in the catheter and a receiver in association with the data acquisition/processing/output device. Accordingly, the electrical signals from the sensor(s) may be viewed by the user, e.g., as output on an electrical monitoring device. The resulting electrical signal may be processed and/or otherwise output for the user so that the user is able to assess tissue contact by the catheter system 10.

What is claimed is:

1. A basket catheter, comprising:
   an outer tubing comprising a distal end;
   a fluid delivery tubing extending from the distal end of the outer tubing, the fluid delivery tubing comprising a proximal fluid delivery port and a distal fluid delivery port; and
   a plurality of splines each connected at a proximal end of the splines to the outer tubing to define a proximal apex and at a distal end of the splines to the fluid delivery tubing to define a distal apex;
   wherein the proximal fluid delivery port is configured to deliver fluid between the plurality of splines and near the proximal apex and wherein the distal fluid delivery port is configured to deliver fluid between the plurality of splines and near the distal apex.

2. The basket catheter of claim 1, wherein the plurality of splines are configured to expand to a deployed position when the splines are actuated and wherein the plurality of splines are configured to collapse to a collapsed position when the splines are deactuated.

3. The basket catheter of claim 2, wherein the distal fluid delivery port is configured to deliver fluid between the plurality of splines and near the distal apex when the plurality of splines are at the deployed and undeployed positions.

4. The basket catheter of claim 2, wherein the proximal fluid delivery port is configured to deliver fluid between the plurality of splines and near the proximal apex when the plurality of splines are at the deployed and undeployed positions.

5. The basket catheter of claim 4, wherein the distal fluid delivery port is configured to deliver fluid between the plurality of splines and near the distal apex when the plurality of splines are at the deployed and undeployed positions.

6. The basket catheter of claim 2, wherein the fluid delivery tubing is operable to be moved in a first direction relative to the outer tubing to actuate the splines to the deployed position, and wherein the fluid delivery tubing is operable to be moved in a second direction relative to the outer tubing to deactuate the splines to the undeployed position.

7. The basket catheter of claim 1, further comprising:
   a seal positioned between the outer tubing and the fluid delivery tubing, the seal configured to prevent fluid ingress back into the outer tubing of the basket catheter.

8. The basket catheter of claim 7, wherein the seal is configured for irrigating between the plurality of splines of the basket catheter.

9. The basket catheter of claim 8, further comprising a membrane provided over at least a portion of the fluid delivery tubing, wherein the seal is positioned at a proximal end of the membrane.

10. A catheter, comprising:
    an elongate body;
    a fluid delivery member extending from the elongate body, the fluid delivery member comprising a proximal fluid delivery opening and a distal fluid delivery opening; and
    a plurality of deflectable members each connected at a distal portion of the deflectable members to the fluid delivery member and at a proximal portion of the deflectable members to one of the elongate body and the fluid delivery member;
    wherein the proximal fluid delivery opening is configured for irrigating between the plurality of deflectable members and towards the proximal portion of at least one of the deflectable members and wherein the distal delivery opening is configured for irrigating between the plurality of deflectable members and towards the distal portion of at least one of the deflectable members.

11. The catheter of claim 10, wherein the plurality of deflectable members are configured to move between a deployed position and a collapsed position, wherein the plurality of deflectable members are expanded when at the deployed position and collapsed when at the collapsed position.

12. The catheter of claim 11, wherein the distal fluid delivery opening is configured for irrigating between the plurality of deflectable members and towards the distal portion of at least one of the deflectable members when the plurality of deflectable members are at the deployed and undeployed positions.

13. The catheter of claim 11, wherein the proximal fluid delivery opening is configured for irrigating between the plurality of deflectable members and towards the proximal portion of at least one of the deflectable members when the plurality of deflectable members are at the deployed and undeployed positions.

14. The catheter of claim 13, wherein the distal fluid delivery opening is configured for irrigating between the plurality of deflectable members and towards the distal portion of at least one of the deflectable members when the plurality of deflectable members are at the deployed and undeployed positions.

15. The catheter of claim 10, wherein the plurality of deflectable members are each connected at the proximal portion of the deflectable members to the elongate body.

16. The catheter of claim 10, wherein the plurality of deflectable members are each connected at the proximal portion of the plurality of deflectable members to the fluid delivery member.

17. An apparatus, comprising:
    a catheter body;
    a plurality of splines each connected at a proximal end of the splines to the catheter body to define a proximal apex and at a distal end of the splines to the catheter body to define a distal apex;
    means for irrigating between the plurality of splines and near the proximal apex; and
    means for irrigating between the plurality of splines and near the distal apex;
    wherein both means for irrigating are provided on a fluid delivery member between the plurality of splines.

18. The apparatus of claim 17, wherein the plurality of splines are configured to perform one of a mapping procedure and an ablation procedure.

19. The apparatus of claim 17, wherein the plurality of splines are configured to move between a deployed position and a collapsed position, wherein the plurality of splines are expanded when at the deployed position and collapsed when at the collapsed position, wherein the means for irrigating between the plurality of splines and near the distal apex is configured to direct fluid between the plurality of splines and near the distal apex when the plurality of splines are at the deployed and undeployed positions.

20. The apparatus of claim 19, wherein the means for irrigating between the plurality of splines and near the proximal apex is configured to direct fluid between the plurality of splines and near the proximal apex when the plurality of splines are at the deployed and undeployed positions.

* * * * *